United States Patent
Wick

(10) Patent No.: US 9,943,503 B1
(45) Date of Patent: Apr. 17, 2018

(54) PHARMACEUTICAL COMPOSITION FOR TREATING BACTERIAL AND VIRAL INFECTIONS

(71) Applicant: Edward Wick, Sussex, WI (US)

(72) Inventor: Edward Wick, Sussex, WI (US)

( * ) Notice: Subject to any disclaimer, the term of this patent is extended or adjusted under 35 U.S.C. 154(b) by 0 days.

(21) Appl. No.: 15/788,114

(22) Filed: Oct. 19, 2017

(51) Int. Cl.
| | |
|---|---|
| A61K 31/59 | (2006.01) |
| A61K 31/34 | (2006.01) |
| A61K 31/07 | (2006.01) |
| A61K 33/32 | (2006.01) |
| A61K 36/8962 | (2006.01) |
| A61K 31/375 | (2006.01) |
| A61K 36/28 | (2006.01) |
| A61K 33/30 | (2006.01) |
| A61K 31/593 | (2006.01) |

(52) U.S. Cl.
CPC ............ *A61K 31/375* (2013.01); *A61K 31/07* (2013.01); *A61K 31/593* (2013.01); *A61K 33/30* (2013.01); *A61K 36/28* (2013.01); *A61K 36/8962* (2013.01)

(58) Field of Classification Search
CPC ..... A61K 31/375; A61K 31/59; A61K 31/601
USPC ................ 514/167, 168, 474, 641, 725, 754
See application file for complete search history.

(56) References Cited

U.S. PATENT DOCUMENTS

| | | | |
|---|---|---|---|
| 9,616,124 B2 | 4/2017 | Nimitz | |
| 2007/0154581 A1 | 7/2007 | Kumar | |
| 2009/0196921 A1* | 8/2009 | Ebel | A61K 35/74 424/457 |
| 2012/0082720 A1* | 4/2012 | Ang | A61K 45/06 424/463 |
| 2013/0017239 A1* | 1/2013 | Viladot Petit | A61K 8/0283 424/401 |
| 2013/0183358 A1* | 7/2013 | Fernandez Botello | A61K 8/14 424/401 |
| 2013/0216596 A1* | 8/2013 | Viladot Petit | A61K 8/11 424/401 |
| 2013/0243889 A1* | 9/2013 | Morehouse | A61K 9/0056 424/725 |
| 2017/0266050 A1* | 9/2017 | Morehouse | A61F 11/00 |
| 2017/0290853 A1* | 10/2017 | Horst | A61K 9/0014 |

OTHER PUBLICATIONS

Yakoot, M and Salem, A Efficacy and safety of a multiherbal formual with vitamin C and zinc (Immumax) in the management of 5 the common cold. International Journal of General Medicine 2011:4, 45-51.
Mayo Clinic Free E-newsletter for dosing of vitamin C.
Mayo Clinic Free E-newsletter for dosing of zinc.
Mayo Clinic Free E-newsletter for dosing of vitamin A.
Mayo Clinic Free E-newsletter for dosing of vitamin D.
Mayo Clinic Free E-newsletter for dosing of Echinacea.
Nahas, R. and Balla A. Complementary and alternative medicine for prevention and treatment of the common cold. Can. Fam. Physician 2011:57, 31-36.
Allan G. M. and Arroll, B. Prevention and treatment of the common cold: making 15 sense of the evidence. CMAJ 2014:186(3), 190-199.

* cited by examiner

*Primary Examiner* — Raymond J Henley, III
(74) *Attorney, Agent, or Firm* — Ming Chow; Sinorica, LLC

(57) ABSTRACT

The present invention relates to a pharmaceutical composition comprising an effective amount of vitamin C, zinc, vitamin A, vitamin D3, garlic, and *Echinacea* to treat bacterial and/or viral infections, and a method for treating bacterial and/or viral infections by orally administering the composition to a patient effective to reduce the symptoms of bacterial and/or viral infections such as colds and influenza.

8 Claims, No Drawings

PHARMACEUTICAL COMPOSITION FOR TREATING BACTERIAL AND VIRAL INFECTIONS

FIELD OF THE INVENTION

The present invention relates generally to a pharmaceutical composition and its use. More specifically, the present invention is a pharmaceutical composition comprising an effective amount of vitamin C, zinc, vitamin A, vitamin D3, garlic and *Echinacea* to treat bacterial or viral infection, and a method for treating bacterial or viral infection by orally administering the composition to a patient effective to reduce the symptoms of bacterial and/or viral infections such as colds and influenza.

BACKGROUND OF THE INVENTION

To treat bacterial infections a variety of antibiotic drugs are available. However, the over-prescription of antibiotics over the past half century gives rise to antibiotic resistant strains of bacteria, such as superbugs (1). More than 400 different viruses are known to cause human diseases. These diseases include, for example, the common cold, influenza, cold sores (Herpes Type 1), genital herpes (Type 2), norovirus, mononucleosis, shingles, hepatitis, dengue, West Nile fever, severe acute respiratory syndrome (SARS), Hantavirus, Ebola, and acquired immunodeficiency syndrome (AIDS), especially in the cases of the common cold and influenza, rapid mutations make it difficult for the body immune system to identify and react to the invading viruses quickly (1). For viral infections in general, and upper respiratory viral infections in particular, effective drugs to hinder reproduction of the infectious agents are much less available. Prescription of anti-flu drugs currently available may reduce the duration of flu by about a day but in many cases do not reduce complications such as pneumonia, and often viruses are resistant to the drugs. As an alternative to conventional pharmaceuticals for treating bacterial or viral infection, interest has grown in the use of certain food supplements for enhancing or stimulating the immune system in the human body (2).

One object of the present invention is to use an alternative composition to enhance or stimulate the immune system of the human body, thus to aid the body's ability to self-repair.

Wellness can be achieved with behavioral and lifestyle modifications utilizing multimodal approaches. For example, with a proper diet, especially vegetables, exercise, and botanical alternatives, this approach strives to improve the physical and emotional wellness of patients. The present inventor has identified certain alternatives, including nutritional and natural mineral supplements as safe and effective alternatives.

The inclusion of prevention and wellness management by physicians as a standard of a patient care will decrease the amount of prescription drugs, hospitalizations, and surgeries. A reduction in prescription drugs and surgeries will result in a substantial decrease in medical errors and will contribute significantly in lowering the cost of health care.

It is therefore an aim of the present invention to provide an alternative composition for treating bacterial or viral infection in a patient, the alternative composition comprising an effective amount of vitamin C, zinc, vitamin A, vitamin D3, garlic and *Echinacea*; and a method for treating bacterial or viral infection in a patient by orally administering the composition to the patient effective to reduce the symptoms of bacterial and/or viral infections such as colds and influenza.

DETAIL DESCRIPTION OF THE INVENTION

The present invention is an oral composition comprising an effective amount of vitamin C, zinc, vitamin A, vitamin D3, garlic and *Echinacea* that is able to treat bacterial or viral infection in a patient. The oral composition is utilized by either adults or children. The oral composition incorporates active ingredients which function cooperatively to enhance or stimulate the immune system of the human body in order to treat bacterial or viral infection.

Vitamin C (ascorbic acid), is a water-soluble vitamin found in the fruit and vegetables, such as citrus fruit (3). It is necessary for iron absorption, wound healing and collagen formation. Vitamin C is also recognized as being important for successful production of neurotransmitters and improvement of glucose metabolism, its deficiency results in the neurological disease of scurvy. Vitamin C, which is associated with immune strengthening, is derived from its ability to enhance the function of the immune system, including antimicrobial and NK cell activities, macrophages, lymphocyte proliferation, chemotaxis and delayed-type hypersensitivity (3). The recommended daily intake by the US food and Nutrition Board of the Institute of Medicine for men more than 18 years old is 90 mg of vitamin C daily; for women more than 18 years old, it is 75 mg daily (4). For treating the common cold, 200 mg to 3 g have been taken by mouth daily for three to five days or longer (4).

Zinc salts have been found to inhibit rhinovirus replication in vitro at concentrations of <0.1 mmole/L, possibly by interfering with rhinovirus protein cleavage (3). It also has been suggested that zinc salts may protect plasma membranes against lysis by cytotoxic agents such as microbial toxins and complement. The proposed protective mechanism is either via immunomodulation or via the binding of zinc ions to rhinovirus surface canyons, thus inhibiting viral interactions with intercellular adhesion molecule-1 (ICAM-1), the site of rhinovirus binding to cells. Because ICAM-1 is also the binding site for leukocyte function associated antigen-1 (LEA-1), the block of LFA-1/ICAM-1 binding has been postulated to possibly suppress inflammation. Several randomized, controlled clinical studies showed a beneficial effect of using zinc for treating the common cold, particularly when zinc is started within the first 24 hours of onset of symptoms (3). The current recommended dietary allowance for zinc taken by mouth is: 11 mg for males 19 years and older; and 8 mg for females 19 years and older (5). For the common cold, doses have ranged from 4.5-24 mg of zinc (gluconate or acetate) in the form of lozenges taken by mouth every 1-3 hours for 3-14 days or until symptoms resolved.

Vitamin A, use as a dietary supplement, for adults and teenagers: oral dosage form (capsules or chewable tablets) has 6-15 mg of beta-carotene (the equivalent of 10,000-25,000 units of vitamin A activity) per day (6). For children: the oral dosage is 3 to 6 mg of beta-carotene (the equivalent of 5,000-10,000 units of vitamin A activity) per day.

Vitamin D is usually in strengths from 50 to 100 international units (IU), it can be found as soft gel, capsules, tablets and liquids (7). The 2010 recommended daily allowance (RDA) is 600 IU for those 1-71 years of age and 800 IU for those over 71 years of age. For immune function, the following doses have been taken by mouth: 40 IU of vitamin D3 daily for 20 years to 100,000 IU of vitamin D3 bimonthly for 12 months, or 10,000 IU daily. For the treatment of respiratory infections, 2000 IU per kilogram body weight has been taken by mouth daily for three days. For viral infections, 800 IU of vitamin D has been taken by mouth daily for two years, followed by 2000 IU of vitamin D daily for 12 months. For viral infection, 60,000 IU has been taken by mouth weekly for six weeks.

Garlic (*Allium sativum*) is one of the oldest medicinal plants used by different cultures (3). The oldest reports of health promoting properties of garlic dated back to the 16$^{th}$ century BC, when over 20 ailments were purported from Egypt to be efficiently cured by garlic. Garlic stimulates the immune system and acts as a natural antibiotic, not harmful to friendly bacteria flora. Many laboratory studies have confirmed the antibacterial, antifungal, antivirus, immune-stimulating, and antioxidant properties of garlic. In 1990, the US National Cancer Institute concluded garlic may be a food with cancer-preventive properties.

*Echinacea*, a member of the Compositae family, is a herb widely used to treat and prevent common illness, as it has been shown to have immune-stimulatory properties (3). Three of the nine species in this family are of medicinal interest (*Echinacea angustifolia, E. pallida* and *E. purpurea*). They are commonly used to treat viral upper respiratory tract infections. *Echinacea* causes an increase in numbers of circulating white blood cells, activation of phagocytosis by human granulocytes, and elevation of body temperature, resulting primarily from the aerial portion of *E. purpurea* and the root portion of *E. pallida*. Previous research suggests that *Echinacea* may be most effective at reducing the severity and duration of the common cold when taken early in the illness, but has little to no preventive benefit. A review of five randomized, clinical trials investigating the immunomodulatory activity of *Echinacea* concluded that *Echinacea* may be an efficacious immune stimulator. For adults (18 years and older), to stimulate the immune system, five 400 mg doses of *Echinacea* have been taken by mouth four times daily for 28 days (8). A dose of 8,000 mg of *Echinacea* has been taken by mouth once daily for 28 days. To treat the common cold in adults, 500-1000 mg of *Echinacea* three times daily for 5-7 days.

In a review of the evidence supporting complementary and alternative medicine for the treatment and prevention of the common cold in adults (9), it indicated that for prevention, vitamin C demonstrated benefit in a large meta-analysis, with possibly increased benefit in patients subjected to cold stress. There is inconsistent evidence for Asian *ginseng* (*Panax ginseng*) and North America *ginseng* (*Panax quinquefolius*). Allicin (an organosulfur compound obtained from garlic) was highly effective in one small trial. For treatment, *Echinacea purpurea* is the most consistently useful variety; it was effective in 5 of 6 trials. Zinc lozenges were effective in 5 of 9 trials, likely owing to dose and formulation issues. Overall, the evidence suggests no benefit from probiotics for prevention or treatment of the common cold.

In another review of the evidence for interventions aimed at preventing and treating the common cold is frequently of poor quality and results are inconsistent (10), it indicated that the best evidence for the prevention of the common cold supports physical interventions (e.g., handwashing) and possibly the use of zinc supplements. The best evidence for non-traditional treatments of common cold supports the use of oral zinc supplements in adults and honey at bed time for cough in children over one year.

A study from Egypt showed that 62 patients with the common cold by giving them either a natural multiherbal formula containing 120 mg of *Echinacea* extract, 100 mg of garlic powder, 200 mg of *Nigella sativa* oil, and 50 mg of *Panax ginseng* extract plus vitamin C 50 mg, and element zinc 7.5 mg (Immumax), or placebo treatment for the duration of their symptoms or a maximum of 14 days (3). The researchers found that while the placebo group's average cold duration was eight (5-9) days, the cold duration of the Immumax group was averaging four (3-6) days. Thus, the study showed the use of combination of multiherbal formula plus vitamin C and zinc is helpful in reducing the duration and severity of common cold symptoms.

It has been reported that a composition and a method for stimulating or enhancing the immune system in a human being (2). The composition comprises a mixture of Manapol (a trademark of Carrington Laboratories, Inc., containing acetylated mannans primarily in the form of mannose), beta-1,3-D-glucan, arabinogalactan, elderberry extract (standardized to about 30% anthocyanins), zinc gluconate and allicin. The composition taken as a food supplement, is particularly useful against infectious diseases and acts as an anti-bacterial, anti-viral or anti-fungal agent.

The reports cited above have showed that the ingredients of vitamin C, zinc, vitamin D3, garlic and *Echinacea*, each ingredient alone or in combination with some other materials have been used to stimulate or enhance the immune system of human body and to treat the common cold. However, there is no report indicating the use of an alternative composition comprising an effective amount of vitamin C, zinc, vitamin A, vitamin D3, garlic and *Echinacea* in the treatment of bacterial or viral infection.

The present invention provides a pharmaceutical composition comprising an effective amount of vitamin C, zinc, vitamin A, vitamin D3, garlic and *Echinacea* that is able to treat bacterial or viral infection in a patient. In one embodiment, the pharmaceutical composition is an oral composition. In another embodiment, the amount of vitamin C is 1100 mg, the amount of zinc is 55 mg, the amount of vitamin A is 50,000 IU, the amount of vitamin D3 is 200 IU, the amount of garlic is 35 IU, and the amount of *Echinacea* is 200 mg in the composition, and the composition in tablet form. In another embodiment, the viral infection is common cold or influenza.

The present invention also provides a method for treating bacterial or viral infection in a patient by orally administering a composition to the patient, wherein the composition comprising an amount of vitamin C, zinc, vitamin A, vitamin D3, garlic and *Echinacea* effective to reduce the symptoms of bacterial and/or viral infections. In one embodiment, the viral infection is common cold and influenza. In another embodiment, the amount of vitamin C is 1100 mg, the amount of zinc is 55 mg, the amount of vitamin A is 50,000 IU, the amount of vitamin D3 is 200 IU, the amount of garlic is 35 IU, and the amount of *Echinacea* is 200 mg in the composition, and the composition is in the tablet form. In another embodiment, the method further comprises an intervention such as adding a proper diet containing vegetables, and exercising.

As used herein, "a" or "an" means one or more (or at least one).

As used herein, "patient" means either a human being, either adults or children using the oral composition.

REFERENCES

1. Samenvatting, U.S. Pat. No. 9,616,124 B2.
2. Kumar et al., US 20070154581.

3. Yakoot, M and Salem, A Efficacy and safety of a multi-herbal formula with vitamin C and zinc (Immumax) in the management of the common cold. International Journal of General Medicine 2011:4, 45-51.
4. Mayo Clinic Free E-newsletter for dosing of vitamin C.
5. Mayo Clinic Free E-newsletter for dosing of zinc.
6. Mayo Clinic Free E-newsletter for dosing of vitamin A.
7. Mayo Clinic Free E-newsletter for dosing of vitamin D.
8. Mayo Clinic Free E-newsletter for dosing of *Echinacea*.
9. Nahas, R. and Balla A. Complementary and alternative medicine for prevention and treatment of the common cold. Can. Fam. Physician 2011:57, 31-36.
10. Allan G. M. and Arroll, B. Prevention and treatment of the common cold: making sense of the evidence. CMAJ 2014:186(3), 190-199.

What is claimed is:

1. A pharmaceutical composition comprising an amount of vitamin C, zinc, vitamin A, vitamin D3, garlic, and *Echinacea* effective to treat bacterial and/or viral infections.

2. The pharmaceutical composition according to claim 1, the composition is an oral composition.

3. The pharmaceutical composition according to claim 1, wherein the amount of vitamin C is 1100 mg, the amount of zinc is 55 mg, the amount of vitamin A is 50,000 IU, the amount of vitamin D3 is 200 IU, the amount of garlic is 35 IU, and the amount of *Echinacea* is 200 mg, and wherein the composition is in tablet form.

4. The pharmaceutical composition according to claim 1, wherein the viral infection is colds or influenza.

5. A method for treating bacterial and/or viral infections by orally administering a pharmaceutical composition comprising an amount of vitamin C, zinc, vitamin A, vitamin D3, garlic, and *Echinacea* to a patient effective to treat bacterial and/or viral infections.

6. The method for treating bacterial and/or viral infections according to claim 5, wherein the amount of vitamin C is 1100 mg, the amount of zinc is 55 mg, the amount of vitamin A is 50,000 IU, the amount of vitamin D3 is 200 IU, the amount of garlic is 35 IU, and the amount of *Echinacea* is 200 mg, and wherein the composition is in tablet form.

7. The method for treating bacterial and/or viral infections according to claim 5, wherein the viral infection is colds or influenza.

8. The method for treating bacterial and/or viral infections according to claim 5, the method further combines with an intervention of using a proper diet containing vegetables and exercising.

* * * * *